US011953672B2

(12) United States Patent
Shinzato et al.

(10) Patent No.: US 11,953,672 B2
(45) Date of Patent: Apr. 9, 2024

(54) OPTICAL UNIT

(71) Applicant: OLYMPUS CORPORATION, Tokyo (JP)

(72) Inventors: Jun Shinzato, Machida (JP); Masaru Inamura, Hachioji (JP); Takehiko Iguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 769 days.

(21) Appl. No.: 17/084,918

(22) Filed: Oct. 30, 2020

(65) Prior Publication Data
US 2021/0048603 A1  Feb. 18, 2021

Related U.S. Application Data

(63) Continuation of application No. PCT/JP2019/003983, filed on Feb. 5, 2019.

(30) Foreign Application Priority Data

May 1, 2018 (JP) ................................. 2018-088337

(51) Int. Cl.
*G02B 7/10* (2021.01)
*G02B 23/24* (2006.01)

(52) U.S. Cl.
CPC ........... *G02B 23/2423* (2013.01); *G02B 7/10* (2013.01); *G02B 23/243* (2013.01); *G02B 23/2484* (2013.01)

(58) Field of Classification Search
CPC .............. G02B 23/2423; G02B 23/243; G02B 23/2484; G02B 7/04; G02B 7/10;
(Continued)

(56) References Cited

U.S. PATENT DOCUMENTS 4,534,624 A * 8/1985 Toda ........................ G02B 7/04
359/823
5,652,922 A * 7/1997 Kohno ..................... G02B 7/10
396/348

(Continued)

FOREIGN PATENT DOCUMENTS

CN  101860167 A  * 10/2010  ........... G02B 27/646
EP  1875291 B1  8/2008

(Continued)

OTHER PUBLICATIONS

J.R. Davis, Alloying: Understanding the Basics 351-416 (2001). (Year: 2001).*

(Continued)

*Primary Examiner* — Cara E Rakowski
*Assistant Examiner* — Wesley Scott Ashton
(74) *Attorney, Agent, or Firm* — Scully, Scott, Murphy & Presser, P.C.

(57) ABSTRACT

An optical unit includes a first barrel, a second barrel, a third barrel, and a position detection unit. Eight magnets including first and second magnets are fixed to the first barrel. A first and second coils are fixed to the second barrel. The position detection unit includes a magnetic sensor configured to detect magnetic fields generated by the first and second magnets and to generate a detection signal having a corresponding relation with a position of the first barrel. The third barrel includes a position defining surface parallel to a moving direction of the first barrel. The position detection unit is fixed to the position defining surface.

16 Claims, 7 Drawing Sheets

(58) Field of Classification Search
CPC ........ G02B 7/021; G02B 7/023; G02B 7/025; G02B 7/026; H02K 41/0356
See application file for complete search history.

(56) References Cited

U.S. PATENT DOCUMENTS

| | | | | |
|---|---|---|---|---|
| 6,091,900 A * | 7/2000 | Kaneda | ............... | G02B 27/646 348/208.11 |
| 6,339,681 B1 * | 1/2002 | Takeshita | ............... | G02B 7/04 396/448 |
| 6,456,444 B1 * | 9/2002 | Yumiki | ................. | G02B 7/102 359/823 |
| 7,154,682 B2 * | 12/2006 | Umezu | ............. | H04N 23/6812 359/557 |
| 7,656,596 B2 * | 2/2010 | Matsumoto | ........... | F16C 29/041 359/822 |
| 7,715,130 B2 * | 5/2010 | Tsai | ......................... | G02B 7/08 359/822 |
| 8,014,658 B2 * | 9/2011 | Huang | ................. | G02B 27/646 359/554 |
| 8,432,478 B2 * | 4/2013 | Yano | ...................... | G03B 17/04 396/75 |
| 9,448,397 B2 * | 9/2016 | Makiyama | ......... | G02B 23/2423 |
| 10,120,181 B2 * | 11/2018 | Kono | ...................... | G02B 7/08 |
| 10,149,606 B2 * | 12/2018 | Iguchi | ............... | A61B 1/00117 |
| 10,151,919 B2 * | 12/2018 | Mitarai | .................... | G02B 7/04 |
| 10,855,898 B2 * | 12/2020 | Nakahara | ............... | H04N 23/55 |
| 11,567,288 B2 * | 1/2023 | Iguchi | ................. | H02K 11/215 |
| 2008/0297922 A1 * | 12/2008 | Lule | .................. | H02K 41/0356 348/345 |
| 2009/0128931 A1 | 5/2009 | Matsumoto | | |
| 2010/0220402 A1 * | 9/2010 | Santo | ..................... | G02B 7/102 359/823 |
| 2013/0314517 A1 * | 11/2013 | Makiyama | ............. | A61B 1/045 348/65 |
| 2016/0213239 A1 * | 7/2016 | Fujii | .................. | A61B 1/00163 |
| 2016/0334608 A1 * | 11/2016 | Hu | .................... | H02K 41/0356 |
| 2017/0065157 A1 * | 3/2017 | Iwasaki | ................. | G03B 13/34 |
| 2017/0258303 A1 | 9/2017 | Iguchi | | |
| 2018/0031800 A1 * | 2/2018 | Iguchi | ............... | G02B 23/2438 |
| 2018/0049621 A1 * | 2/2018 | Iguchi | ................. | A61B 1/0019 |
| 2018/0081164 A1 * | 3/2018 | Ito | ...................... | A61B 1/00188 |
| 2021/0096320 A1 * | 4/2021 | Otsuka | ................... | H04N 23/55 |

FOREIGN PATENT DOCUMENTS

| | | | | | |
|---|---|---|---|---|---|
| JP | 06201978 A | * | 7/1994 | | |
| JP | H06-221868 A | | 8/1994 | | |
| JP | 07225333 A | * | 8/1995 | | |
| JP | H08-248297 A | | 9/1996 | | |
| JP | 2003035860 A | * | 2/2003 | | |
| JP | 2004258689 A | * | 9/2004 | ............ | G02B 7/102 |
| JP | 2006-292959 A | | 10/2006 | | |
| JP | 2008-289315 A | | 11/2008 | | |
| JP | 2013-246135 A | | 12/2013 | | |
| JP | 2017111193 A | * | 6/2017 | | |
| WO | 2006/109587 A1 | | 10/2006 | | |
| WO | 2016/051838 A1 | | 4/2016 | | |
| WO | 2016/098225 A1 | | 6/2016 | | |

OTHER PUBLICATIONS

Hall-effect Position Sensors with Sealed Housing, 2014, pp. 1-17 [online], [retrieved Aug. 19, 2023], retrieved from the Internet <URL: https://prod-edam.honeywell.com/content/dam/honeywell-edam/sps/siot/en-us/products/sensors/magnetic-sensors/value-added-packaged-sensors/103sr-series/documents/. (Year: 2014).*
Machine English Translation of JP 08-248297 A obtained from J-Plat and filed with copy of JP 08-248297A. (Year: 2023).*
Roger Cicala, A Look at Electromagnetic Focusing, 2016, pp. 1-38 [online], [retrieved Feb. 18, 2024], retrieved from the Internet <URL: https://www.lensrentals.com/blog/2016/04/a-look-at-electromagnetic-focusing?>. (Year: 2016).*
International Search Report dated May 14, 2019 issued in PCT/JP2019/003983.

* cited by examiner

OPTICAL UNIT

CROSS REFERENCE TO RELATED APPLICATION

This application is a continuation application of PCT/JP2019/003983 filed on Feb. 5, 2019 and claims benefit of Japanese Application No. 2018-088337 filed in Japan on May 1, 2018, the entire contents of which are incorporated herein by this reference.

BACKGROUND OF THE INVENTION

1. Field of the Invention

The present invention relates to an optical unit that includes a movable lens barrel that is a lens barrel for holding a lens, and that can move by interaction between a magnet and a coil.

2. Description of the Related Art

Generally, an image pickup apparatus including an optical unit including a lens and an image pickup device is provided in an insertion portion of an endoscope. Further, a configuration of the optical unit which moves the lens in an optical axis direction is known. A voice coil motor is used as a mechanism for moving the lens, for example. In an optical unit using a voice coil motor, a movable lens barrel for holding a lens is configured to move by interaction between a magnetic field generated by a magnet and a magnetic field generated by a coil.

A position of the lens can be detected using a magnetic sensor, for example. International Publication No. 2016/051838 discloses a lens apparatus that detects a position of a movable lens by detecting a magnetic flux of a magnet fixed to a lens moving frame using a Hall IC arranged in a housing box of a lens barrel.

International Publication No. 2016/098225 discloses an optical unit including a magnetic detector configured to detect a magnetic field generated by a magnet of a voice coil motor. The magnetic detector is fixed to a coil of the voice coil motor with an adhesive.

SUMMARY OF THE INVENTION

An optical unit according to an aspect of the present invention includes: a first barrel that holds a lens; a second barrel that involves the first barrel such that the first barrel is movable along an optical axis of the lens; a third barrel that involves at least a part of the second barrel and includes a position defining surface parallel to a moving direction of the first barrel; a magnet fixed to the first barrel; a coil fixed to the second barrel and configured to generate a magnetic field for moving the first barrel by interacting with a magnetic field generated by the magnet; and a position detection unit including a magnetic sensor configured to detect the magnetic field generated by the magnet and to generate a detection signal having a corresponding relation with a position of the first barrel, a substrate including a sensor mounting surface facing the position defining surface, the magnetic sensor being mounted on the sensor mounting surface, and a base member that defines a distance between the position defining surface and the sensor mounting surface, wherein the base member is fixed to the sensor mounting surface with a first adhesive.

An optical unit according to another aspect of the present invention includes: a first barrel that holds a lens; a second barrel that involves the first barrel such that the first barrel is movable along an optical axis of the lens; a third barrel that involves at least a part of the second barrel; a magnet fixed to the first barrel; a coil fixed to the second barrel and configured to generate a magnetic field for moving the first barrel by interacting with a magnetic field generated by the magnet; and a position detection unit including a magnetic sensor configured to detect the magnetic field generated by the magnet and to generate a detection signal having a corresponding relation with a position of the first barrel, wherein the third barrel includes a position defining surface parallel to a moving direction of the first barrel, the position detection unit further includes a fixing portion, the fixing portion is fixed to the position defining surface with an adhesive, and the magnetic sensor is not in contact with any part of the adhesive.

DETAILED DESCRIPTION OF THE PREFERRED EMBODIMENT

An embodiment of the present invention will be described below with reference to the drawings.

(Configuration of Endoscope)

Figure 1:
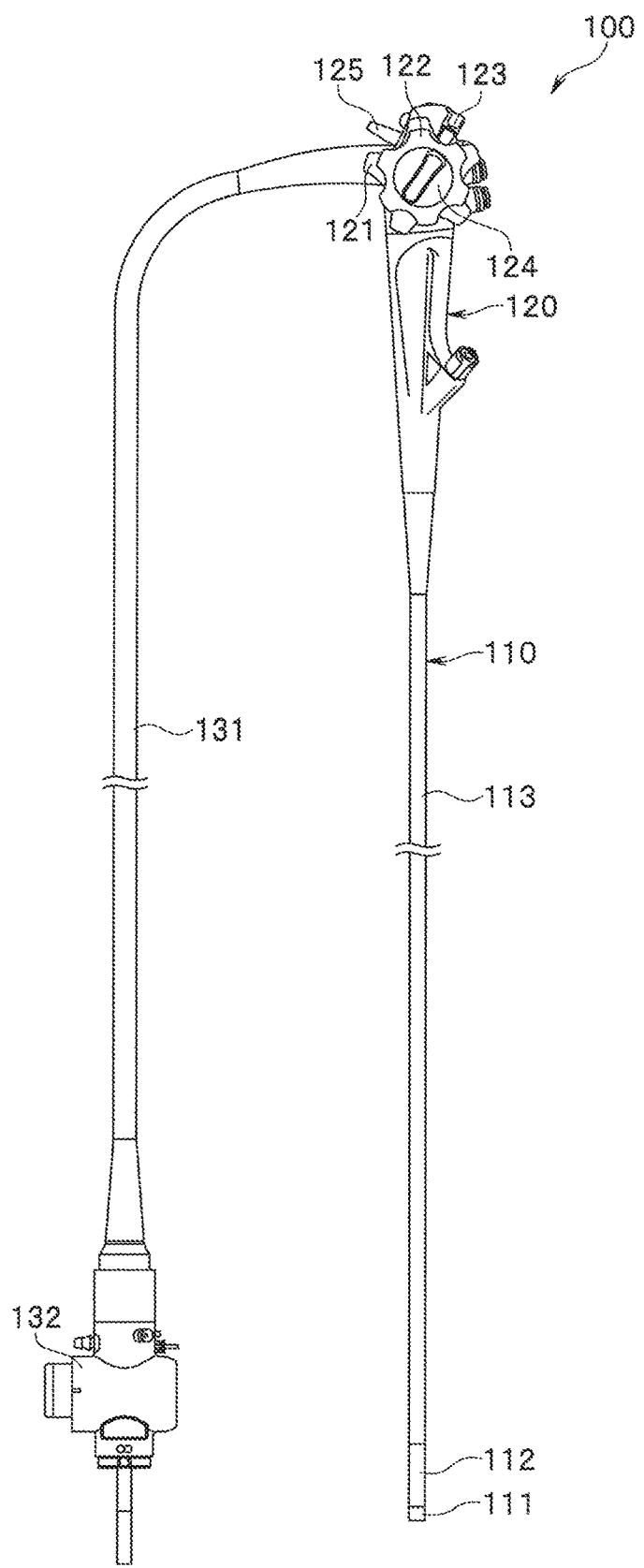
FIG. 1 is a side view showing a configuration of an endoscope including an optical unit according to an embodiment of the present invention.

First, a configuration of an endoscope including an optical unit according to an embodiment of the present invention will be described. FIG. 1 is an explanatory diagram showing an endoscope 100. The endoscope 100 includes an insertion portion 110 inserted into a subject, an operation portion 120 consecutively connected to a proximal end of the insertion portion 110, a universal cord 131 extending from the operation portion 120, and a connector 132 provided at a distal end of the universal cord 131. The endoscope 100 is connected to an external apparatus such as a control apparatus and a lighting apparatus (which are not shown) via the connector 132.

The insertion portion 110 has an elongated shape, and includes a distal end portion 111 located at a distal end of the insertion portion 110, a bending portion 112 configured to be bendable, and a flexible tube portion 113 having flexibility. The distal end portion 111, the bending portion 112, and the flexible tube portion 113 are connected in this order from the distal end side of the insertion portion 110.

The operation portion 120 is provided with an up and down bending operation knob 121 and a left and right bending operation knob 122. The bending portion 112 of the insertion portion 110 is configured to be bent, for example, in four directions of up, down, left, and right by a rotation operation of the up and down bending operation knob 121 and the left and right bending operation knob 122. The up and down bending operation knob 121 bends the bending portion 112 in an up and down direction. The left and right bending operation knob 122 bends the bending portion 112 in the left and right direction.

The operation portion 120 is further provided with a fixing lever 123, a fixing knob 124, and a zoom lever 125. The fixing lever 123 fixes a rotation position of the up and down bending operation knob 121. The fixing knob 124 fixes a rotation position of the left and right bending operation knob 122. The zoom lever 125 moves a first barrel, which will be described below.

The endoscope 100 further includes an image pickup apparatus provided at the distal end portion 111 of the insertion portion 110. The image pickup apparatus includes an optical unit 1 according to the present embodiment and an image pickup device (not shown) configured to pick up an image of an object. The image pickup device is configured by a CCD or a CMOS, for example.

(Configuration of Optical Unit)

Figure 2:
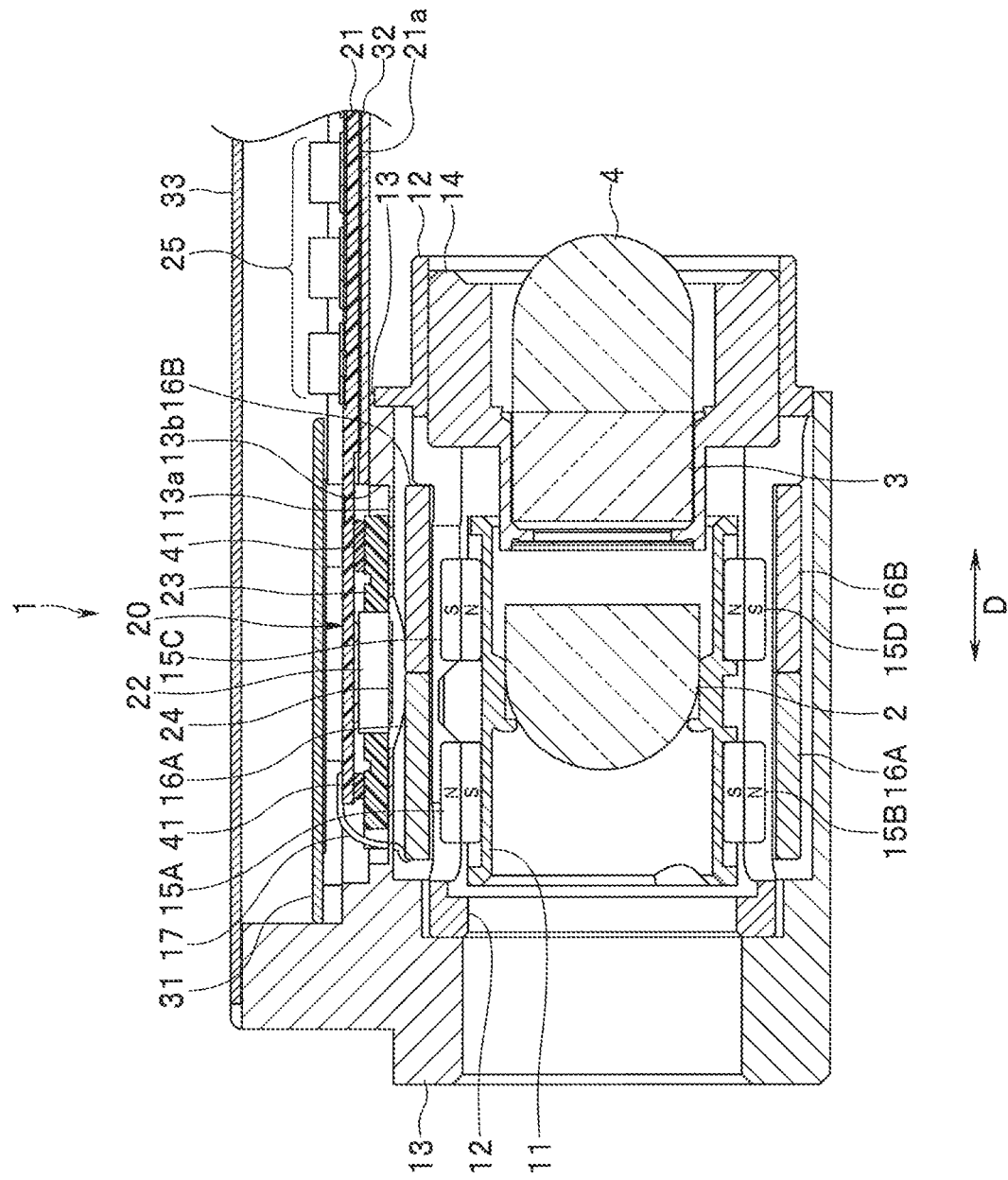
FIG. 2 is a cross-sectional view showing the optical unit according to the embodiment of the present invention.
Figure 3:
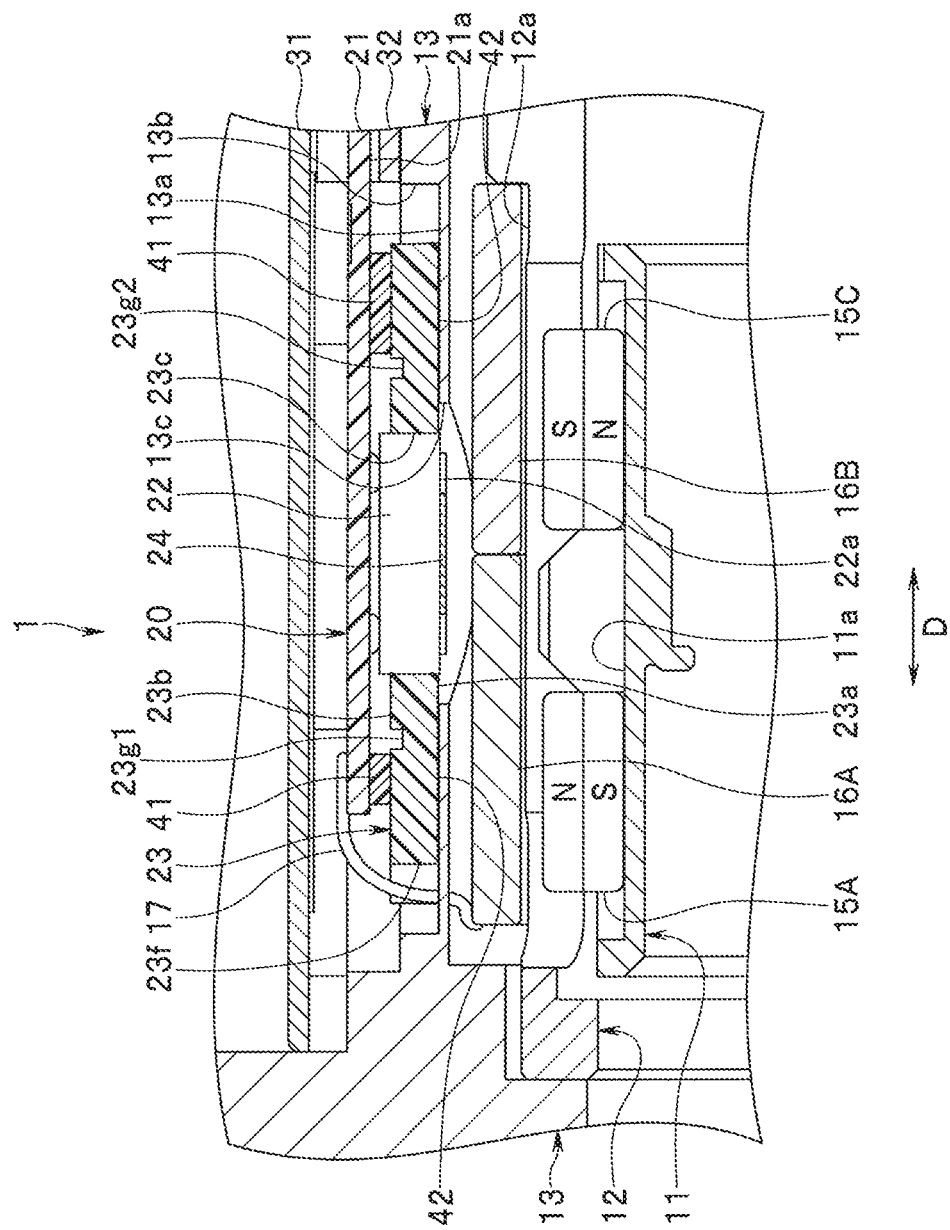
FIG. 3 is a partially enlarged cross-sectional view of constituent components shown in FIG. 2.

A configuration of the optical unit 1 will be described below in detail with reference to FIGS. 2 and 3. FIG. 2 is a cross-sectional view showing the optical unit 1. FIG. 3 is a partially enlarged cross-sectional view of constituent components shown in FIG. 2.

As shown in FIG. 2, the optical unit 1 includes a movable lens 2 and fixed lenses 3 and 4. Note that in FIG. 3, the movable lens 2 and the fixed lenses 3 and 4 are not shown. The movable lens 2 and the fixed lenses 3 and 4 are arranged to be aligned with each other in the same direction. The image pickup device is configured to pick up an image of the object via the movable lens 2 and the fixed lenses 3 and 4. In the example shown in FIG. 2, the movable lens 2 is located on the object side with respect to the fixed lenses 3 and 4. Note that the configuration of the lenses of the optical unit 1 is not limited to the example shown in FIG. 2.

As shown in FIG. 2, a direction D is defined herein. The movable lens 2 and the fixed lenses 3 and 4 are arranged in such a posture that extending directions of respective optical axes coincide with the direction D.

As shown in FIGS. 2 and 3, the optical unit 1 further includes a first barrel 11, a second barrel 12, a third barrel 13, and a fourth barrel 14 which have cylindrical shapes extending in the direction D, respectively. The first barrel 11 holds the movable lens 2 therein. The fourth barrel 14 holds the fixed lenses 3 and 4 therein. Each of the first barrel 11, the second barrel 12, the third barrel 13, and the fourth barrel 14 is formed of a metal material such as stainless steel.

The second barrel 12 involves the first barrel 11 and the fourth barrel 14. The first barrel 11 is involved in the second barrel 12 closer to the object side than the fourth barrel 14, and is movable along the optical axis of the movable lens 2, that is, in the direction D. The fourth barrel 14 is fixed to the second barrel 12 closer to the image pickup device side than the first barrel 11.

The third barrel 13 involves at least a part of the second barrel 12. FIG. 2 shows an example in which the third barrel 13 involves a part of the second barrel 12. Further, the third barrel 13 has a position defining surface 13a. The position defining surface 13a is a surface parallel to a central axis of the third barrel 13. In the present embodiment, the central axis of the third barrel 13 is parallel to a moving direction of the first barrel 11, that is, the direction D. Therefore, the position defining surface 13a is also a surface parallel to the moving direction of the first barrel 11, that is, the direction D. In the present embodiment, particularly, the position defining surface 13a is a flat surface.

The optical unit 1 further includes magnets and coils that configure a voice coil motor. In the present embodiment, the optical unit 1 includes four first magnets and four second magnets fixed to the first barrel 11 as magnets configuring the voice coil motor. In the present embodiment, as shown in FIG. 3, a step 11a is formed on an outer peripheral portion of the first barrel 11. The four first magnets are fixed to the step 11a at intervals of about 90° around the axis of the first barrel 11. Note that in FIG. 2, two first magnets 15A and 15B of the four first magnets are located on opposite sides with the central axis of the first barrel 11 therebetween. Although not shown, a portion of the step 11a to which the first magnet is fixed may be a flat surface.

The four second magnets are located on the image pickup device side with respect to the four first magnets and are fixed to the step 11a at intervals of about 90° around the axis of the first barrel 11. Note that in FIG. 2, two second magnets 15C and 15D of the four second magnets are located on opposite sides with the central axis of the first barrel 11 therebetween. Although not shown, a portion of the step 11a to which the second magnet is fixed may be a flat surface.

The four first magnets and the four second magnets contain N-poles and S-poles, respectively. In the first magnets, the N-pole is located farther from the central axis of the first barrel 11, and the S-pole is located closer to the central axis of the first barrel 11. In the second magnets, the arrangement of the N-pole and the S-pole is opposite to the arrangement of the N-pole and the S-pole in the first magnet. In other words, in the second magnets, the N-pole is located closer to the central axis of the first barrel 11, and the S-pole is located farther from the central axis of the first barrel 11.

In the present embodiment, the optical unit 1 includes, as the coils configuring the voice coil motor, a first coils 16A and a second coil 16B fixed to the second barrel 12. The first coil 16A and the second coil 16B are arranged to be aligned with each other in the direction D. In the present embodiment, as shown in FIG. 3, a winding portion 12a, around which a winding wire is wound, is formed on the outer peripheral portion of the second barrel 12. The first coil 16A is configured by the winding wire wound around the winding portion 12a in the axial direction of the second barrel 12. The second coil 16B is located on the image pickup device side with respect to the first coil 16A, and is configured by the winding wire wound around the winding portion 12a in the axial direction of the second barrel 12.

The first coil 16A and the second coil 16B are configured such that direction of currents flowing through the winding wire in the axial direction of the second barrel 12 are opposite to each other. Specifically, for example, the first coil 16A and the second coil 16B may be configured such that winding directions of the winding wires configuring the first coil 16A and the second coil 16B are opposite to each other. Alternatively, the first coil 16A and the second coil 16B may be configured such that the winding directions of the winding wires configuring the first coil 16A and the second coil 16B are the same as each other and the directions of the currents flowing through the winding wires are opposite to each other.

The optical unit 1 further includes a position detection unit 20 and a magnetic member 31 which are fixed to the third barrel 13. The magnetic member 31 is made of a magnetic material, and generates an attractive force with the first magnet 15A and the second magnet 15C. The first barrel 11 is attracted to the magnetic member 31 by the attractive force described above. Although not shown, a portion of an outer peripheral surface of the first barrel 11 facing the magnetic member 31 contacts an inner peripheral surface of the second barrel 12. The first barrel 11 moves in the direction D, that is, along the optical axis of the movable lens 2 in a state where a part of the outer peripheral surface of the first barrel 11 contacts the inner peripheral surface of the second barrel 12.

A part of the position detection unit 20 is located between the first and second magnets 15A and 15C and the magnetic member 31. A configuration of the position detection unit 20 will be described below.

The optical unit 1 further includes a support member 32 and a protective member 33 which are fixed to the third barrel 13. The support member 32 is used to support another part of the position detection unit 20. The protective member 33 covers the position detection unit 20 and the magnetic member 31.

(Configuration of Position Detection Unit)

Figure 4:
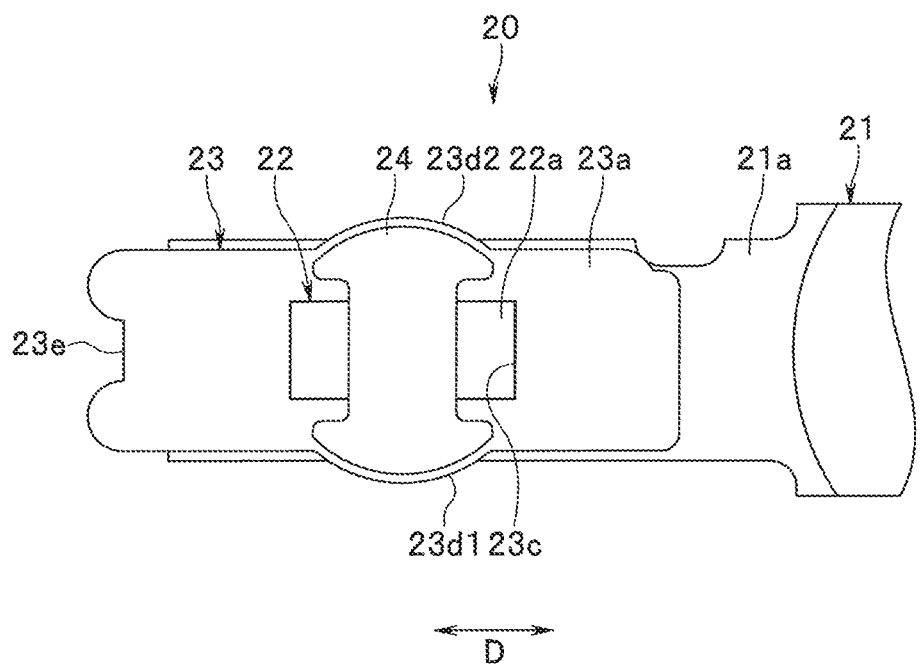
FIG. 4 is a plan view showing a position detection unit in the embodiment of the present invention.

The configuration of the position detection unit 20 will be described below with reference to FIGS. 2 to 4. FIG. 4 is a plan view showing the position detection unit 20. The position detection unit 20 includes a substrate 21, a magnetic sensor 22, a base member 23, a restriction member 24, and a circuit unit 25.

As shown in FIGS. 2 to 4, the substrate 21 includes a sensor mounting surface 21a. FIG. 4 shows the position detection unit 20 as seen from the sensor mounting surface 21a. The position detection unit 20 is fixed to the third barrel 13 in a posture in which the sensor mounting surface 21a faces the position defining surface 13a of the third barrel 13. The first and second magnets 15A and 15C are located at positions facing the sensor mounting surface 21a. An example of the substrate 21 to be used includes a flexible substrate.

The magnetic sensor 22 is mounted on the sensor mounting surface 21a of the substrate 21 by soldering, for example. The magnetic sensor 22 includes a facing surface 22a farthest from the sensor mounting surface 21a. The facing surface 22a is also a surface facing the first and second magnets 15A and 15C.

The magnetic sensor 22 detects magnetic fields generated by the first and second magnets 15A and 15C, and generates a detection signal having a corresponding relation with the position of the first barrel 11. The magnetic sensor 22 includes a magnetic detection element configured to detect the magnetic fields generated by the first and second magnets 15A and 15C. An example of the magnetic detection element to be used includes a magnetoresistance effect element or a Hall element.

The base member 23 is fixed to the sensor mounting surface 21a of the substrate 21 with a first adhesive 41, and is fixed to the position defining surface 13a with a second adhesive 42. The base member 23 defines a distance between the position defining surface 13a and the sensor mounting surface 21a. Further, the base member 23 is also a fixed member fixed to the position defining surface 13a with an adhesive. As the first and second adhesives 41 and 42, adhesives having a high viscosity before curing are preferably used.

In the present embodiment, the base member 23 has a plate-like shape which is long in the direction D. As shown in FIGS. 3 and 4, the base member 23 includes a facing surface 23a farthest from the sensor mounting surface 21a, a bonding surface 23b facing the sensor mounting surface 21a, and a housing hole 23c in which the magnetic sensor 22 is housed. The facing surface 23a is bonded to the position defining surface 13a with the second adhesive 42 and is parallel to the position defining surface 13a. The bonding surface 23b is bonded to the sensor mounting surface 21a with the first adhesive 41. The housing hole 23c penetrates the base member 23 from the facing surface 23a to the bonding surface 23b. The magnetic sensor 22 is located in the housing hole 23c. In the present embodiment, the magnetic sensor 22 is not in contact with any part of the first and second adhesives 41 and 42.

The base member 23 is made of a non-magnetic material. An example of the non-magnetic material includes a resin material. In the present embodiment, since the base member 23 is made of a resin material, it is possible to prevent a short-circuit due to the contact of a conductive pattern provided on the surface of the magnetic sensor 22 and the solder used to mount the magnetic sensor 22 with the third barrel 13.

As shown in FIGS. 2 and 3, the third barrel 13 further includes a housing portion 13b that houses the magnetic sensor 22 and the base member 23. The housing portion 13b has a shape corresponding to the base member 23. In the present embodiment, the position defining surface 13a is a bottom surface of the housing portion 13b. The shape of the base member 23 and the shape of the third barrel 13 will be described in more detail below.

As shown in FIGS. 2 to 4, the restriction member 24 contacts the facing surface 22a of the magnetic sensor 22 and is fixed to the facing surface 23a of the base member 23. In the present embodiment, the restriction member 24 has a flat plate shape. As shown in FIG. 4, a portion, which contacts the facing surface 22a of the magnetic sensor 22, of the restriction member 24, contacts only a part of the facing surface 22a of the magnetic sensor 22.

The restriction member 24 restricts the position of the magnetic sensor 22 such that the facing surface 22a of the magnetic sensor 22 does not protrude from the facing surface 23a of the base member 23. In other words, the restriction member 24 restricts the position of the magnetic sensor 22 in a direction perpendicular to the facing surface 23a of the base member 23. In the present embodiment, the facing surface 23a of the base member 23 is bonded to the position defining surface 13a with the second adhesive 42. Accordingly, since the position of the magnetic sensor 22 is defined in the direction perpendicular to the facing surface 23a of the base member 23, the position of the magnetic sensor 22 is also defined with respect to the position defining surface 13a.

The restriction member 24 is formed of a non-magnetic material. From the viewpoint of increasing strength of the restriction member 24, the non-magnetic material forming the restriction member 24 is preferably a non-magnetic metal material.

The circuit unit 25 includes an electronic component used to drive the magnetic sensor 22. The electronic component is mounted on a surface of the substrate 21 opposite to the sensor mounting surface 21a.

The circuit unit 25 may further include an electronic component used to drive the first and second coils 16A and 16B configuring the voice coil motor. Such an electronic component is electrically connected to the first and second coils 16A and 16B by a lead 17 shown in FIGS. 2 and 3 and a wiring (not shown) formed on the substrate 21.

(Shape of Third Barrel)

Figure 5:
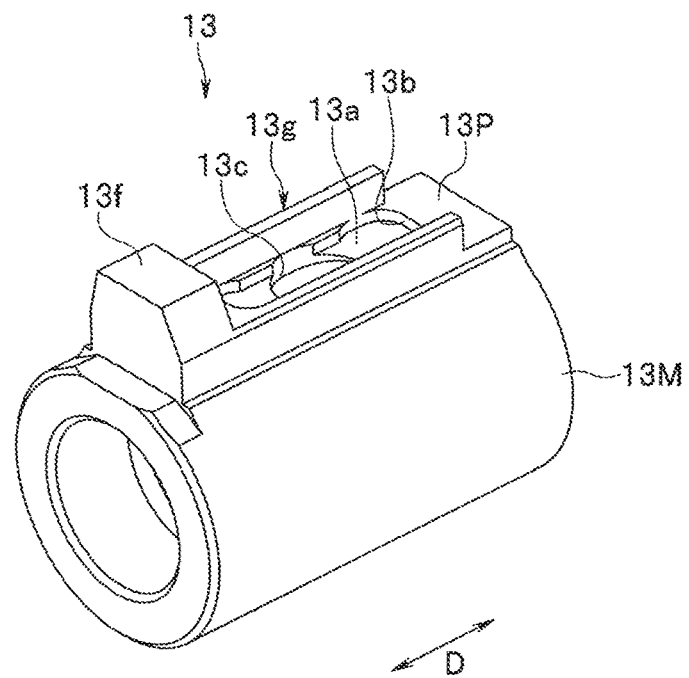
FIG. 5 is a perspective view showing a third barrel in the embodiment of the present invention.
Figure 6:
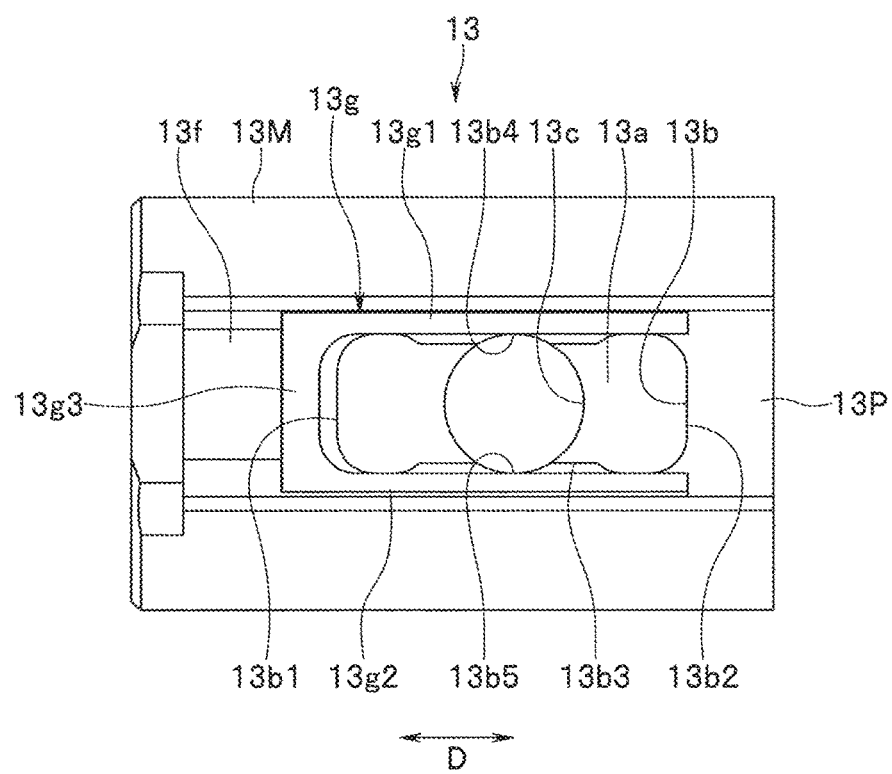
FIG. 6 is a plan view showing the third barrel in the embodiment of the present invention.

A shape of the third barrel 13 will be described in detail below with reference to FIGS. 3, 5, and 6. FIG. 5 is a perspective view showing the third barrel 13. FIG. 6 is a plan view showing the third barrel 13. As shown in FIG. 5, the third barrel 13 includes a cylindrical main body portion 13M extending in the direction D and a flat plate portion 13P coupled to an outer peripheral portion of the main body portion 13M. In the present embodiment, a central axis of the main body portion 13M is referred to as the central axis of the third barrel 13. The second barrel 12 (see FIG. 2) is involved in the main body portion 13M.

The flat plate portion 13P includes a flat surface parallel to the central axis of the main body portion 13M. The housing portion 13b is configured by a groove formed on the flat surface of the flat plate portion 13P. The bottom surface of the housing portion 13b, that is, the position defining surface 13a is parallel to the flat surface of the flat plate portion 13P.

The third barrel 13 further includes a protruding portion 13f and a frame portion 13g. The protruding portion 13f is coupled to the flat plate portion 13P in the vicinity of an end portion of the flat plate portion 13P on the object side (a left side in FIG. 6). The protruding portion 13f has a protruding shape from the flat surface of the flat plate portion 13P.

The frame portion 13g is coupled to the flat plate portion 13P on the side of the image pickup device (a right side in FIG. 6) with respect to the protruding portion 13f. The frame portion 13g includes two sidewalls 13g1 and 13g2 and a coupling portion 13g3. Each of the sidewalls 13g1 and 13g2 has a long shape in the direction D. In addition, the sidewalls 13g1 and 13g2 are arranged at predetermine intervals in a direction parallel to the position defining surface 13a and a direction orthogonal to the direction D (an up and down direction in FIG. 6). The coupling portion 13g3 couples the protruding portion 13f to the sidewalls 13g1 and 13g2.

The housing portion 13b is located between the sidewalls 13g1 and 13g2. The position detection unit 20 (see FIGS. 2 to 4) is fixed to the position defining surface 13a such that the magnetic sensor 22 and the base member 23 are housed in the housing portion 13b and a part of the substrate 21 is located between the two sidewalls 13g1 and 13g2. The magnetic member 31 (see FIGS. 2 and 3) is fixed to the frame portion 13g, for example.

The third barrel 13 further includes a through hole 13c that penetrates the position defining surface 13a, that is, the bottom surface of the housing portion 13b from the magnetic sensor 22 toward the central axis of the third barrel 13, that is, the central axis of the main body portion 13M. A shape of the through hole 13c (hereinafter, referred to as a planar shape of the through hole 13c) as viewed in the direction from the magnetic sensor 22 toward the central axis of the main body portion 13M may be larger than the shape of the magnetic sensor 22 as viewed in the same direction.

In the examples shown in FIGS. 5 and 6, the planar shape of the through hole 13c is circular. Note that the planar shape of the through hole 13c may be oval or rectangular.

The entire restriction member 24 may be located in the through hole 13c. In this case, the restriction member 24 is not in contact with the position defining surface 13a.

As shown in FIG. 6, the housing portion 13b of the third barrel 13 includes two wide width parts 13b1 and 13b2 arranged at a predetermined interval in the direction D and a narrow width part 13b3 located between the wide width parts 13b1 and 13b2. A dimension of the narrow width part 13b3 in the direction parallel to the position defining surface 13a and the direction orthogonal to the direction D (up and down direction in FIG. 6) is smaller than maximum dimensions of the wide width parts 13b1 and 13b2 in the same directions except for two concave parts to be described below.

The through hole 13c is formed so as to penetrate a bottom surface of the narrow width part 13b3. The housing portion 13b further includes two concave parts 13b4 and 13b5 formed in the narrow width part 13b3. The concave parts 13b4 and 13b5 are arranged at a predetermined interval in the direction parallel to the position defining surface 13a and the direction orthogonal to the direction D (up and down direction in FIG. 6). Each of the concave parts 13b4 and 13b5 has a shape corresponding to an outer edge of the through hole 13c, that is, an arc shape.

(Shape of Base Member)

Figure 7:
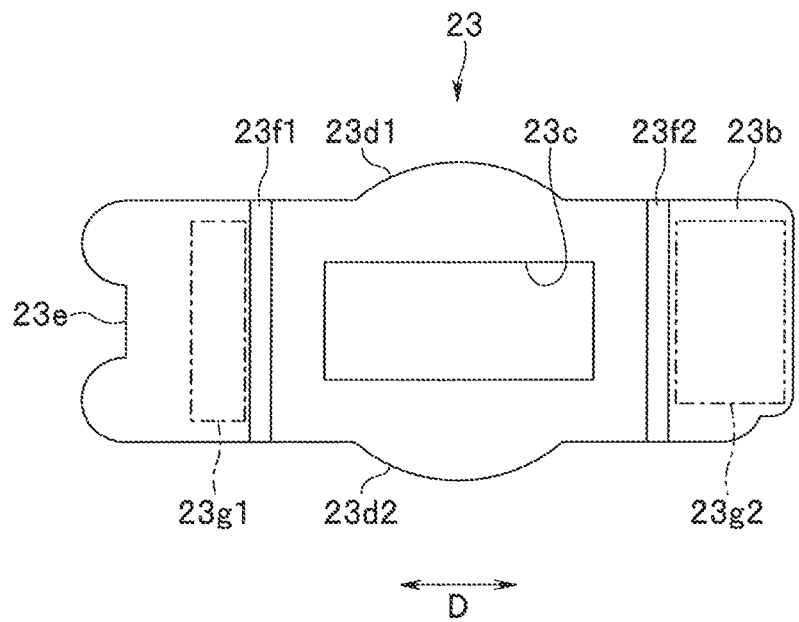
FIG. 7 is a plan view showing a base member in the embodiment of the present invention.

A shape of the base member 23 will be described in detail below with reference to FIGS. 3, 4, and 7. FIG. 7 is a plan view showing the base member 23. FIG. 7 shows the base member 23 as viewed from the bonding surface 23b. As shown in FIGS. 4 and 7, the base member 23 includes two convex parts 23d1 and 23d2 and a concave part 23e in addition to the facing surface 23a, the bonding surface 23b, and the housing hole 23c.

Each of the convex parts 23d1 and 23d2 protrudes in a direction parallel to the facing surface 23a, that is, in the direction parallel to the position defining surface 13a and the direction orthogonal to the direction D (up and down direction in FIG. 7). Each of outer edges of the convex parts 23d1 and 23d2 has a shape corresponding to the concave parts 13b4 and 13b5 of the housing portion 13b, that is, an arc shape. In the present embodiment, particularly, the outer edge (arc) of the convex part 23d1 and the outer edge (arc) of the convex part 23d2 are parts of one virtual circle on a virtual flat surface parallel to the facing surface 23a. Note that the concave parts 13b4 and 13b5 may have a shape corresponding to the convex parts 23d1 and 23d2. The convex parts 23d1 and 23d2 are fitted into the concave parts 13b4 and 13b5, respectively, in a state where the position detection unit 20 is fixed to the position defining surface 13a.

The concave part 23e is provided at an end of the base member 23 on the object side (a left side in FIG. 7). The concave part 23e is used to pass through the lead 17.

The base member 23 further includes two grooves 23f1 and 23f2 formed on the bonding surface 23b in the vicinity of the housing hole 23c. As shown in FIG. 7, each of the grooves 23f1 and 23f2 has a long shape in the direction parallel to the bonding surface 23b and the direction orthogonal to the direction D (up and down direction in FIG. 7).

In addition, as shown in FIG. 7, the bonding surface 23b includes a bonding part 23g1 located farther from the housing hole 23c than the groove 23f1 and a bonding part 23g2 located farther from the housing hole 23c than the groove 23f2. The bonding parts 23g1 and 23g2 are regions to which the first adhesive 41 is applied before curing. The first adhesive 41 bonds the sensor mounting surface 21a and the bonding parts 23g1 and 23g2.

(Operation of Method of Moving First Barrel)

A method of moving the first barrel 11 will be described below with reference to FIG. 2. The first coil 16A and the second coil 16B generate magnetic fields for moving the first barrel 11 by interaction between the magnetic fields generated by the four first magnets and the four second magnets. The magnetic field for moving the first barrel 11 can be generated when a current flows to the first coil 16A and the second coil 16B. The four first magnets face each other on the first coil 16A. The four second magnets face each other on the second coil 16B. Due to the interaction between the magnetic fields generated by the four first magnets and the magnetic field generated by the first coil 16A, a first driving force acts on the first barrel 11 in the direction parallel to the direction D. Similarly, due to the interaction between the magnetic fields generated by the four second magnets and the magnetic field generated by the second coil 16B, a second driving force acts on the first barrel 11 in the direction parallel to the direction D.

As described above, the first coil 16A and the second coil 16B are configured such that the directions of the currents are opposite to each other, and the N-pole and the S-pole are reversely arranged in the first magnet and the second magnet. Therefore, a direction of the first driving force coincides with a direction of the second driving force by Flemings's Left Hand Law.

When the directions of the currents flowing through the first coil 16A and the second coil 16B are reversed, the direction of the first driving force and the direction of the second driving force are also reversed. Thus, the first barrel 11 can move toward the object side or the image pickup device side in the direction D. The moving direction of the first barrel 11 can be indicated by the zoom lever 125 (see FIG. 1), for example.

(Operation and Effects)

Operation and effects of the optical unit 1 according to the present embodiment will be described below. In the present embodiment, the position detection unit 20 is fixed to the position defining surface 13a of the third barrel 13. The position of the position defining surface 13a in the third barrel 13 is uniquely determined. Therefore, when the position detection unit 20 is fixed to the position defining surface 13a, the position of the magnetic sensor 22 included in the position detection unit 20 can be accurately defined. In the present embodiment, particularly, the position defining surface 13a is parallel to the moving direction (direction D) of the first barrel 11. Thereby, according to the present embodiment, the position of the magnetic sensor 22 can be accurately defined in the direction orthogonal to the moving direction (direction D) of the first barrel 11, and as a result, the distance between the first and second magnets 15A and 15C and the magnetic sensor 22 can be accurately defined in the same direction. Therefore, according to the present embodiment, a change in output characteristics of the magnetic sensor 22 can be prevented.

In the present embodiment, particularly, the position defining surface 13a is a flat surface. Thus, according to the present embodiment, the position of the magnetic sensor 22 can be defined more accurately.

In the present embodiment, since the first and second magnets 15A and 15C serve as both the magnets for generating the magnetic field detected by the magnetic sensor 22 and the magnet configuring the voice coil motor, it is not necessary to provide magnets for position detection. Thereby, according to the present embodiment, the increase in the number of constituent components can be prevented.

In the present embodiment, the magnetic sensor 22 is mounted on the substrate 21, but is not directly fixed to the position defining surface 13a. In other words, in the present embodiment, the base member 23 fixed to the substrate 21 with the first adhesive 41 is fixed to the position defining surface 13a with the second adhesive 42, so that the position detection unit 20 is fixed to the position defining surface 13a. If the magnetic sensor 22 is directly fixed to the position defining surface 13a with an adhesive, the position of the magnetic sensor 22 may shift or stress may be applied to the magnetic sensor 22 due to shrinkage caused by the curing of the adhesive, and the output characteristics of the magnetic sensor 22 change.

On the other hand, in the present embodiment, the magnetic sensor 22 is not in contact with any part of the first and second adhesives 41 and 42. Thus, according to the present embodiment, the change in the output characteristics of the magnetic sensor 22 can be prevented.

In the present embodiment, the magnetic sensor 22 is located in the housing hole 23c of the base member 23, and the grooves 23f1 and 23f2 are formed in the vicinity of the housing hole 23c. The first adhesive 41 before curing is applied not to the housing hole 23c, but to the bonding parts 23g1 and 23g2 located farther from the grooves 23f1 and 23f2. The grooves 23f1 and 23f2 function as an adhesive reservoir capable of accumulating the first adhesive 41 before curing. Thereby, according to the present embodiment, it is possible to prevent the first adhesive 41 before curing from adhering to the magnetic sensor 22 when the position detection unit 20 is manufactured.

In the present embodiment, the restriction member 24 is provided in contact with the facing surface 22a of the magnetic sensor 22 and fixed to the facing surface 23a of the base member 23. As described above, the restriction member 24 is configured to define the position of the magnetic sensor 22. Even in such a configuration, according to the present embodiment, the position of the magnetic sensor 22 can be defined more accurately.

In the present embodiment, the restriction member 24 is formed of the non-magnetic material. Thus, according to the present embodiment, it is possible to prevent the intensity of the magnetic field detected by the magnetic sensor 22 from decreasing as compared with a case where the restriction member 24 is formed of a magnetic material, and as a result, to prevent the sensitivity of the magnetic sensor 22 from decreasing.

In the present embodiment, the third barrel 13 is provided with the through hole 13c that penetrates the position defining surface 13a from the magnetic sensor 22 toward the central axis of the third barrel 13. Even in such a configuration, according to the present embodiment, it is possible to prevent the intensity of the magnetic field detected by the magnetic sensor 22 from decreasing, and as a result, to prevent the sensitivity of the magnetic sensor 22 from decreasing.

In the present embodiment, the third barrel 13 includes the housing portion 13b that houses the magnetic sensor 22 and the base member 23. The position defining surface 13a is the bottom surface of the housing portion 13b. In the present embodiment, particularly, the base member 23 includes the convex parts 23d1 and 23d2, and the housing portion 13b includes the concave parts 13b4 and 13b5 having the shape corresponding to the convex parts 23d1 and 23d2. From such facts, according to the present embodiment, the position detection unit 20 can be accurately fixed to the position defining surface 13a.

There may be a case where the posture of the magnetic sensor 22 is rotated from a desired posture and fixed to the substrate 21 when viewed in a direction perpendicular to the sensor mounting surface 21a of the substrate 21. In this case, the posture of the base member 23 is also rotated from a desired posture and fixed to the substrate 21 according to the posture of the magnetic sensor 22 when viewed in the direction perpendicular to the sensor mounting surface 21a of the substrate 21. From the viewpoint of preventing interference between the constituent components, the position detection unit 20 is preferably fixed to the position defining surface 13a in a posture in which a longitudinal direction of the substrate 21 coincides with a longitudinal direction of the third barrel 13. However, when the magnetic sensor 22 and the base member 23 rotated as described above are housed in the housing portion 13b and the position detection unit 20 is fixed to the position defining surface 13a, the longitudinal direction of the substrate 21 tilts from the longitudinal direction of the third barrel 13.

On the other hand, in the present embodiment, each of the concave parts 13b4 and 13b5 and the convex parts 23d1 and 23d2 has an arc shape. Thereby, according to the present embodiment, the magnetic sensor 22 and the base member 23 rotate in the axial direction of the virtual circle including the arc such that the longitudinal direction of the substrate 21 coincides with the longitudinal direction of the third barrel 13, and thus the position detection unit 20 can be fixed to the position defining surface 13a.

In the present embodiment, the magnetic sensor 22 detects components (hereinafter, referred to as detection components), in the direction orthogonal to the moving direction (direction D) of the first barrel 11 and the direction perpendicular to the sensor mounting surface 21a of the substrate 21, of the magnetic fields generated by the first and second magnets 15A and 15C. The intensity of the detection component detected by the magnetic sensor 22 changes depending on the position of the magnetic sensor 22 in the direction described above, but the posture of the magnetic sensor 22 is not affected when viewed in the direction perpendicular to the sensor mounting surface 21a of the substrate 21. Therefore, even when the magnetic sensor 22 rotates and the position detection unit 20 is fixed as described above, the output characteristics of the magnetic sensor 22 do not change.

In the present embodiment, the magnetic member 31 is provided to generate an attractive force with the first and second magnets 15A and 15C. Thereby, according to the present embodiment, it is possible to prevent the first barrel 11, to which the first and second magnets 15A and 15C are fixed, from tilting, and as a result, to define more accurately the distance between the first and second magnets 15A and 15C and the magnetic sensor 22 in the direction orthogonal to the moving direction (direction D) of the first barrel 11.

In the present embodiment, the magnetic sensor 22 is located between the first and second magnets 15A and 15C and the magnetic member 31. Thereby, according to the present embodiment, it is possible to prevent the intensity of the magnetic field detected by the magnetic sensor 22 from decreasing as compared with the case where the magnetic member 31 is located between the first and second magnets 15A and 15C and the magnetic sensor 22, and as a result, to prevent the sensitivity of the magnetic sensor 22 from decreasing.

Further, according to the present invention, the magnetic member 31 can shield the noise magnetic field to be applied to the magnetic sensor 22. Even in such a configuration, according to the present embodiment, it is possible to prevent the output characteristics of the magnetic sensor 22 from changing.

In the present embodiment, the portion of the restriction member 24 being in contact with the facing surface 22a of the magnetic sensor 22 contacts only a part of the facing surface 22a of the magnetic sensor 22. Accordingly, in the present embodiment, the restriction member 24 covers only a part of the housing hole 23c of the base member 23. Thereby, according to the present embodiment, it is possible to confirm the position of the magnetic sensor 22 and to fix the base member 23, to which the restriction member 24 is fixed, to the substrate 21 when the position detection unit 20 is created.

[Modification]

Figure 8:
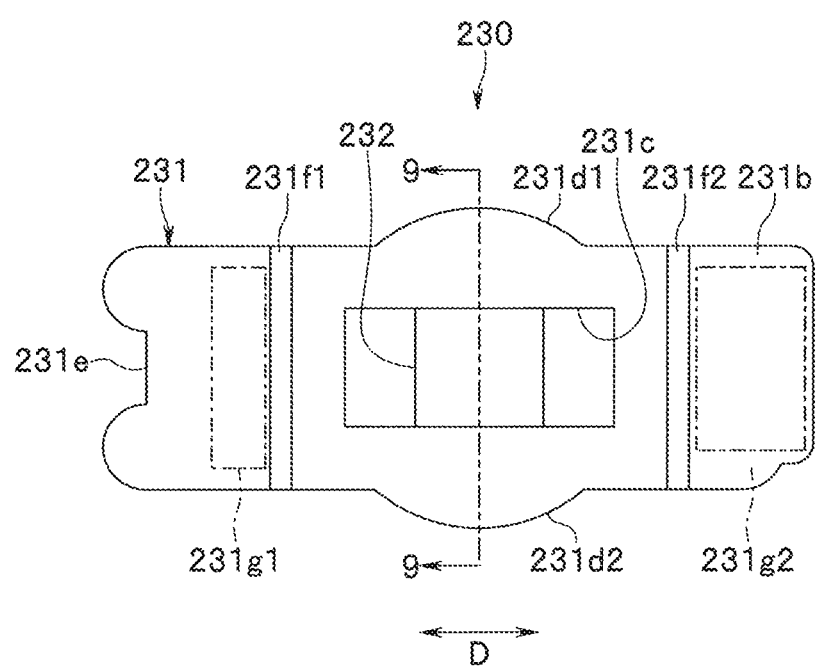
FIG. 8 is a plan view showing a base member according to a modification in the embodiment of the present invention.
Figure 9:
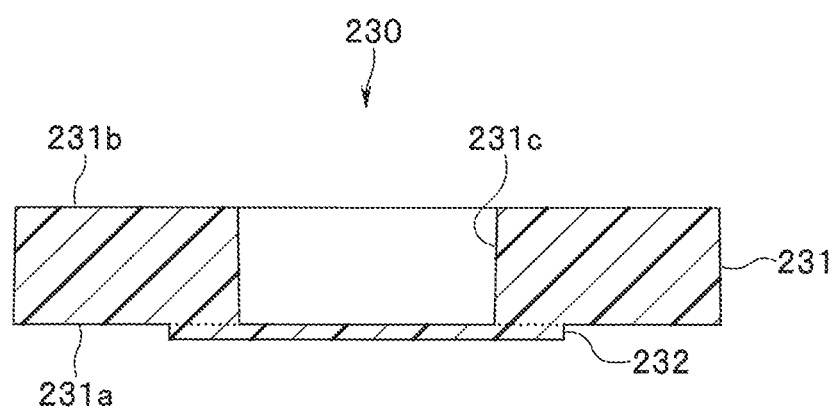
FIG. 9 is a cross-sectional view showing the base member according to the modification in the embodiment of the present invention.

A modification of the base member 23 will be described below with reference to FIGS. 8 and 9. FIG. 8 is a plan view showing a base member 230 according to the modification. FIG. 9 is a cross-sectional view showing the base member 230 according to the modification. FIG. 9 shows a cross section of a position taken along line 9-9 in FIG. 8.

The base member 230 according to the modification includes a main body portion 231 and a restriction portion 232. In FIG. 9, a boundary between the main body portion 231 and the restriction portion 232 is shown by a dotted line. The main body portion 231 is a portion fixed to the sensor mounting surface 21a (see FIGS. 2 and 3) of the substrate 21. A shape and an arrangement of the main body portion 231 are basically the same as the shape and the arrangement of the base member 23. However, the main body portion 231 includes an end part 231a farthest from the sensor mounting surface 21a (see FIGS. 2 and 3), instead of the facing surface 23a of the base member 23.

The main body portion 231 further includes a bonding surface 231b, a housing hole 231c, two convex parts 231d1 and 231d2, a concave part 231e, and two grooves 231f1 and 231f2. The bonding surface 231b includes bonding parts 231g1 and 231g2. Shapes, arrangements, and functions of the bonding surface 231b, the housing hole 231c, the convex parts 231d1 and 231d2, the concave part 231e, the grooves 231f1 and 231f2, and the bonding parts 231g1 and 231g2 are the same as the shapes, the arrangements, and the functions of the bonding surface 23b, the housing hole 23c, the convex parts 23d1 and 23d2, the concave part 23e, the grooves 23f1 and 23f2, and the bonding parts 23g1 and 23g2 of the base member 23, respectively.

In the modification, the magnetic sensor 22 (see FIGS. 2 and 3) is located in the housing hole 231c of the main body portion 231. The restriction portion 232 is in contact with the facing surface 22a of the magnetic sensor 22 and is coupled to the end part 231a of the main body portion 231. In the present embodiment, the restriction portion 232 has a flat plate shape. Although not shown, a part of the restriction portion 232 being in contact with the facing surface 22a of the magnetic sensor 22 is in contact with only a part of the facing surface 22a of the magnetic sensor 22.

In the modification, since the main body portion 231 and the restriction portion 232 are integrally molded, the number of constituent components can be reduced.

The present invention is not limited to the embodiment described above, and various changes and modifications can be made without changing the gist of the present invention. For example, a portion of the surface of the base member 23 applied with the first and second adhesives 41 and 42 before curing may be subjected to surface treatment to increase adhesive strength. Examples of the surface treatment include Tetra-Etch (registered trademark) treatment, filing, and plasma cleaning treatment.

In addition, the grooves 231f1 and 231f2 may be interposed between the bonding surface 23b of the base member 23 and the sensor mounting surface 21a of the substrate 21 instead of being provided in the base member 23, and a spacer may be provided to surround the housing hole 23c of the base member 23. The spacer can be formed by insert molding a member to be the spacer into the base member 23, for example. Since the spacer is provided, the distance between the base member 23 and the substrate 21 can be accurately defined. In addition, the first adhesive 41 before curing is applied to the outside of the spacer. In this case, the first adhesive 41 may be applied to be in contact with the spacer. In this case, since the bonding surface 23b, the sensor mounting surface 21a, and the spacer are bonded to each other with the first adhesive 41, the adhesive strength between the base member 23 and the substrate 21 can be improved as compared to a case where the spacer is not provided.

The position detection unit 20 may be configured without the base member 23. In this case, the position detection unit 20 may be fixed to the position defining surface 13a in such a manner that a part of the substrate 21 is used as a fixed portion, the facing surface 22a of the magnetic sensor 22 is brought into contact with an abutting part which is a part of the position defining surface 13a, and the fixed portion is fixed to the other part of the position defining surface 13a of the third barrel 13 with an adhesive. In this case, no part of the adhesive is preferably in contact with the magnetic sensor 22. The abutting part and the other part of the position defining surface 13a may be different parts of one surface, or may be two surfaces having different distances from the central axis of the third barrel 13. Out of the abutting part and the other part of the position defining surface 13a, at least the abutting part is preferably a flat surface.

What is claimed is:

1. An optical unit comprising:
a first barrel that holds a lens;
a second barrel that involves the first barrel such that the first barrel is movable along an optical axis of the lens;
a third barrel that involves at least a part of the second barrel and includes a position defining surface parallel to a moving direction of the first barrel;
a magnet fixed to the first barrel;
a coil fixed to the second barrel and configured to generate a magnetic field for moving the first barrel by interacting with a magnetic field generated by the magnet; and
a position detection unit including a magnetic sensor configured to detect the magnetic field generated by the magnet and to generate a detection signal having a corresponding relation with a position of the first barrel, a substrate including a sensor mounting surface facing the position defining surface, the magnetic sensor being mounted on the sensor mounting surface, and a base member that defines a distance between the position defining surface and the sensor mounting surface, wherein
the base member is fixed to the sensor mounting surface with a first adhesive, and
the first adhesive is not interposed between the position defining surface and the magnetic sensor.

2. The optical unit according to claim 1, wherein the magnetic sensor is not in contact with any part of the first adhesive.

3. The optical unit according to claim 2, wherein
the base member includes a bonding surface facing the sensor mounting surface, a housing hole that houses the magnetic sensor, and at least one groove formed on the bonding surface in a vicinity of the housing hole,
the bonding surface includes a bonding part located farther from the housing hole than the at least one groove, and
the first adhesive bonds the sensor mounting surface and the bonding part.

4. The optical unit according to claim 1, wherein
the base member is fixed to the position defining surface with a second adhesive, and
the magnetic sensor is not in contact with any part of the second adhesive.

5. The optical unit according to claim 1, wherein
each of the magnetic sensor and the base member includes a facing surface farthest from the sensor mounting surface, and
the position detection unit further includes a restriction member in contact with the facing surface of the magnetic sensor and fixed to the facing surface of the base member.

6. The optical unit according to claim 5, wherein a portion of the restriction member in contact with the facing surface of the magnetic sensor is in contact with only a part of the facing surface of the magnetic sensor.

7. The optical unit according to claim 5, wherein the restriction member is made of a non-magnetic material.

8. The optical unit according to claim 1, wherein
the magnetic sensor includes a facing surface farthest from the sensor mounting surface,
the base member includes a main body portion fixed to the sensor mounting surface and a restriction portion,
the main body portion includes an end part farthest from the sensor mounting surface, and
the restriction portion is in contact with the facing surface of the magnetic sensor and is coupled to the end part of the main body portion.

9. The optical unit according to claim 8, wherein a portion of the restriction portion in contact with the facing surface of the magnetic sensor is in contact with only a part of the facing surface of the magnetic sensor.

10. The optical unit according to claim 1, wherein
the third barrel further includes a housing portion that houses the magnetic sensor and the base member, and
the position defining surface is a bottom surface of the housing portion.

11. The optical unit according to claim 10, wherein
the base member includes a facing surface farthest from the sensor mounting surface and at least one convex part protruding in a direction parallel to the facing surface, and
the housing portion includes at least one concave part having a shape corresponding the at least one convex part.

12. The optical unit according to claim 10, wherein the third barrel further includes a through hole that penetrates the position defining surface from the magnetic sensor toward a central axis of the third barrel.

13. The optical unit according to claim 1, further comprising:
a magnetic member fixed to the third barrel and configured to generate an attractive force with the magnet.

14. The optical unit according to claim 13, wherein the magnetic sensor is located between the magnet and the magnetic member.

15. An optical unit comprising:
a first barrel that holds a lens;
a second barrel that involves the first barrel such that the first barrel is movable along an optical axis of the lens;
a third barrel that involves at least a part of the second barrel;
a magnet fixed to the first barrel;
a coil fixed to the second barrel and configured to generate a magnetic field for moving the first barrel by interacting with a magnetic field generated by the magnet; and
a position detection unit including a magnetic sensor configured to detect the magnetic field generated by the magnet and to generate a detection signal having a corresponding relation with a position of the first barrel, wherein the third barrel includes a position defining surface parallel to a moving direction of the first barrel, the position detection unit further includes a fixed portion, the fixed portion is fixed to the position defining surface with an adhesive, the magnetic sensor is not in contact with any part of the adhesive, and the adhesive is not interposed between the position defining surface and the magnetic sensor.

16. The optical unit according to claim 15, further comprising:

a magnetic member fixed to the third barrel and configured to generate an attractive force with the magnet.

* * * * *